United States Patent
Vrba

[11] Patent Number: 6,048,350
[45] Date of Patent: Apr. 11, 2000

[54] SEGMENTED BALLOON DELIVERY SYSTEM

[75] Inventor: Anthony C. Vrba, Maple Grove, Minn.

[73] Assignee: Scimed Life Systems, Inc., Maple Grove, Minn.

[21] Appl. No.: 09/332,786

[22] Filed: Jun. 14, 1999

[51] Int. Cl.⁷ .................................................. A61M 29/02
[52] U.S. Cl. ............................................................ 606/108
[58] Field of Search ................................. 606/108, 194, 606/198; 604/101

[56] References Cited

U.S. PATENT DOCUMENTS

| | | |
|---|---|---|
| 4,927,412 | 5/1990 | Menasche . |
| 5,290,306 | 3/1994 | Trotta et al. . |
| 5,409,495 | 4/1995 | Osborn . |
| 5,522,882 | 6/1996 | Gaterud et al. . |
| 5,545,132 | 8/1996 | Fagan et al. . |
| 5,607,444 | 3/1997 | Lam ......................................... 606/194 |
| 5,620,457 | 4/1997 | Pinchasik et al. ...................... 606/194 |
| 5,647,857 | 7/1997 | Anderson et al. . |
| 5,792,172 | 8/1998 | Fischell et al. . |
| 5,797,948 | 8/1998 | Dunham . |
| 5,807,327 | 9/1998 | Green et al. . |
| 5,836,965 | 11/1998 | Jendersee et al. . |
| 5,855,565 | 1/1999 | Bar-Cohen et al. .................... 606/198 |
| 5,935,135 | 8/1999 | Bramfitt et al. . |
| 5,976,155 | 11/1999 | Foreman et al. ........................ 606/108 |
| 5,976,181 | 11/1999 | Whelan et al. .......................... 606/194 |

FOREIGN PATENT DOCUMENTS 0 688 580 A1  12/1995  European Pat. Off. .

*Primary Examiner*—Jeffrey A. Smith
*Assistant Examiner*—Eduanto C. Robert
*Attorney, Agent, or Firm*—Vidas, Arrett & Steinkraus, P.A.

[57] ABSTRACT

The present invention utilizes a balloon catheter which has a plurality of balloon elements or segments which are carried by the catheter in a stent mounting region. The balloon elements are spaced and arranged longitudinally relative to the catheter, within the stent mounting region, and provide at least one space between the balloon elements. An expandable stent may be carried by the balloon catheter in the stent mounting region. When mounted to the balloon catheter the stent is in an unexpanded diameter and when inflated by the balloon elements the stent will expand to an expanded diameter sufficient for seating into a body vessel. At least one stent mounting body is positioned in each of the spaces between the individual balloon elements. These stent mounting bodies extend radially from the catheter between the balloon elements and have a predetermined size which is less than the expanded stent diameter. The stent mounting bodies directly receive and secure the stent in the unexpanded diameter to the balloon catheter, while providing for minimal contact between the balloon elements and the stent.

14 Claims, 2 Drawing Sheets

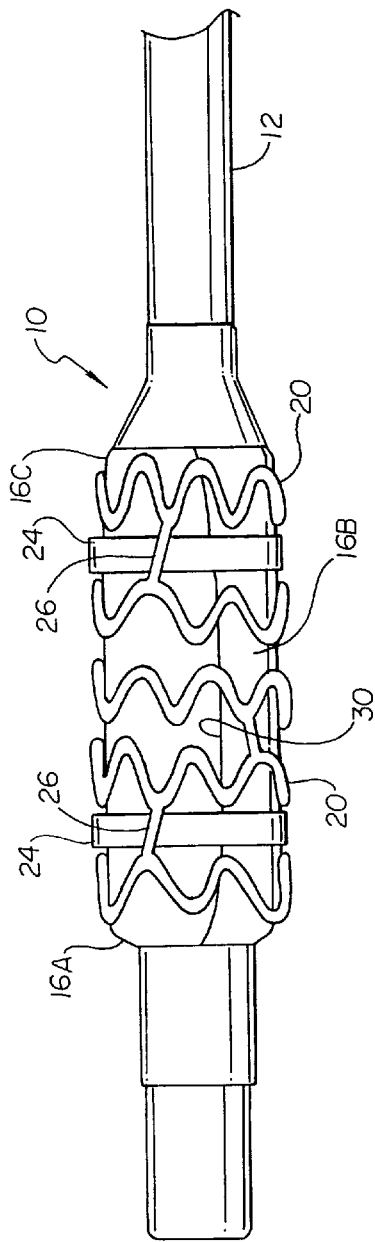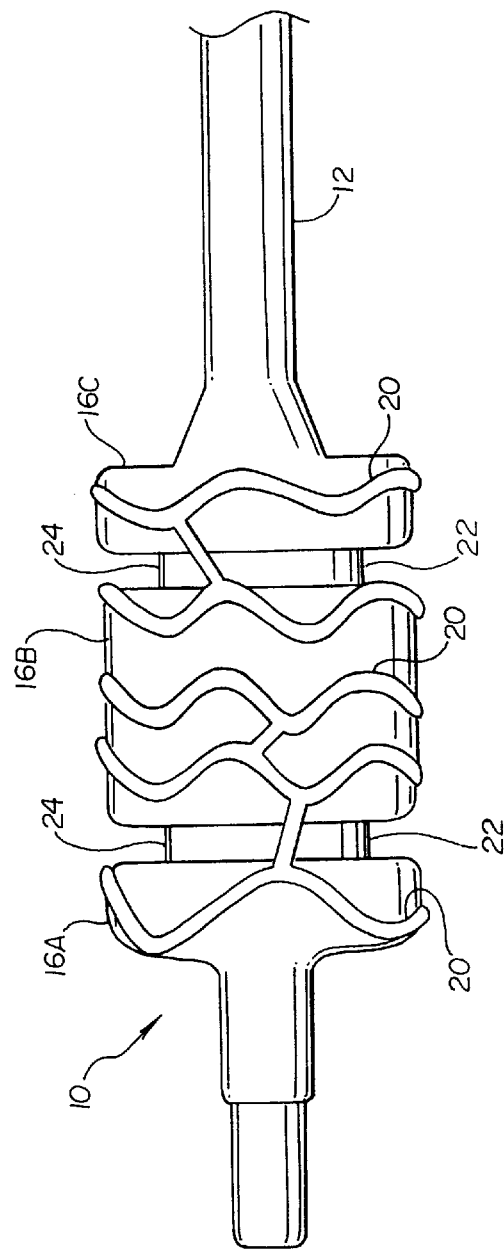

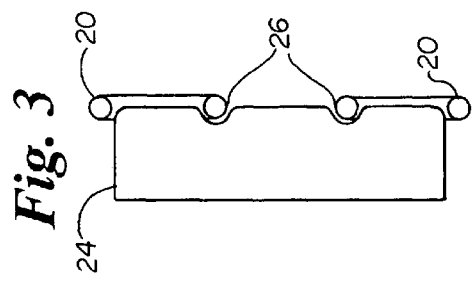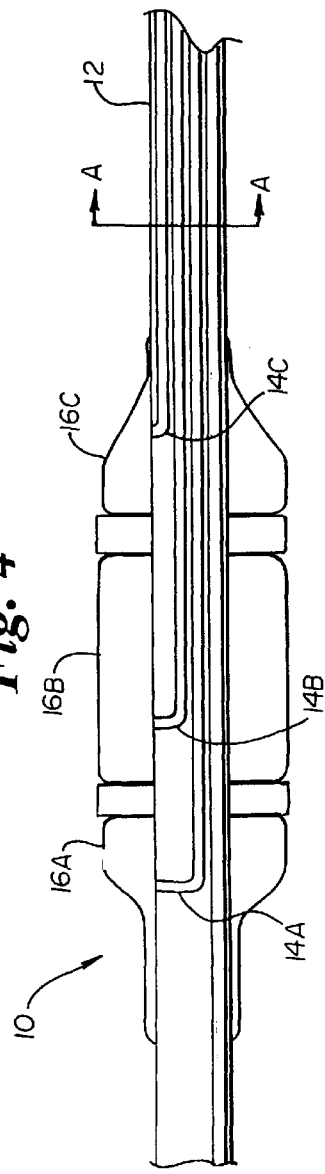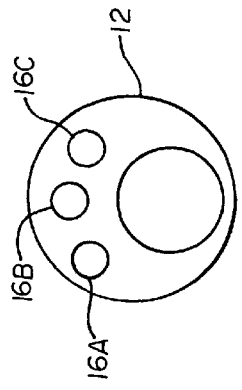

SEGMENTED BALLOON DELIVERY SYSTEM

BACKGROUND OF THE INVENTION

This invention relates to a balloon catheter for use in delivering a medical device such as a stent to a desired body location, such as in a blood vessel. More specifically, this invention relates to a stent mounting region on a balloon catheter which has multiple balloon elements while are separated by spaces. Contained within the spaces between the balloon elements are stent mounting bodies which extend radially and act to receive and secure a stent, in its pre-delivered crimped form, to the balloon catheter.

In balloon expansion of a stent it is important that the stent be accurately positioned over the body portion of a balloon. Failure to properly position the stent over the balloon may result in an unintended non-uniform expansion of the stent. Furthermore, improper positioning of the stent with respect to the balloon during inflation may result in improper final placement of the stent within the body vessel. Failure to keep the stent securely positioned during balloon expansion may cause the expanded stent to shift in position or drift within the vessel prior to the final seating of the expanded stent.

The present invention addresses the above problems by ensuring proper securement and positioning of the stent over the balloon throughout the expansion process by utilizing a segmented balloon or multiple balloon elements respectively interspaced with a stent mounting body or bodies.

It is well known in the stent delivery art that a stent delivery apparatus, such as a balloon catheter, should have as low a profile as possible. However, due to the design and construction of many stents, the delivery apparatus will often require that additional protective layers be added to the catheter in order to protect the expansion balloon from being damaged by the stent during inflation, as well as to protect the anatomy of the vessel from being hooked or torn by the stent as it is inserted into the body. As such, numerous delivery catheters have employed multiple layer balloons, and complex sheath arrangements all of which undesirably increase the diameter of the delivery catheter.

One such multiple layer balloon catheter for delivering a stent is U.S. Pat. No. 5,807,327 to Green et al (Green), incorporated herein by reference. Green discloses a stent delivery catheter having a balloon (126) with three layers. A first or inner layer (138) is a burst resistant layer which has a second layer (140) disposed exteriorly of the first layer (138). Because of problems associated with the high coefficient of friction of the second layer (140) a third layer (142) may be wholly or partially added to the second layer (140). Green uses an excessive number of balloon layers to ensure that the balloon is uniformly inflated. The multiple layers of Green and other similar multiple layer balloon catheters have a greater profile than is desirable.

U.S. Pat. No. 5,647,847 to Anderson et al (Anderson), which is incorporated herein by reference, discloses a sheath for holding a device in a desired position against a balloon catheter for delivery in the lumen of a patient. By adding a sheath such as that which is shown in Anderson, an additional layer is added to the balloon catheter thereby undesirably increasing the profile of the catheter.

The present invention provides a low profile catheter capable of properly expanding and seating a stent. The low profile balloon catheter of the present invention utilizes one or more stent mounting bodies to secure the stent to the catheter, the bodies being arranged so that the balloon has minimal contact with the potentially sharp edges of the stent. The stent mounting bodies of the present invention provide the feature of ensuring that the stent is accurately and securely positioned on the balloon catheter with respect to the balloon, thereby ensuring proper expansion and positioning of the stent during balloon inflation.

BRIEF SUMMARY OF THE INVENTION

The present invention is directed broadly to a balloon catheter including a stent mounting body or bodies which receive the stent distally, allowing the balloon to avoid distal contact with the unexpanded stent.

The stent mounting bodies may be designed to mate with the open structures typical of most stents. The stent mounting bodies may be individually configured on a stent-by-stent basis to mate with the numerous and often uniquely shaped open structure typical of stents. The stent mounting bodies may be configured to act as simple supports or guides for the stent during inflation thereby preventing the stent from shifting position during expansion. Furthermore, by mounting the stent directly to the stent mounting bodies, as opposed to mounting the stent upon a balloon having internal mounting bodies, allows the balloon to avoid the potentially sharp edges of the stent's open structures which could otherwise rupture the balloon prior to or during inflation. The stent mounting bodies may also be configured to form a mechanical lock with the open structures of a given stent type, or form a lock that selectively releases portions of the stent during expansion.

The stent mounting bodies may be comprised of a compressible or elastic material so as to deform under the stent to provide support and holding for it.

In order to accommodate the presence of stent mounting bodies along the central shaft of a catheter, the balloon is formed in multiple individual balloon elements with spaces between each balloon element. The balloon elements may be individual balloons per se or segmented portions of a single balloon or any combination thereof. The stent mounting bodies are located within the spaces that separate the balloon elements. The stent mounting bodies extend radially away from the catheter.

The stent receiving portion(s) of the stent mounting bodies may be configured with unique end caps or heads which will act to form mechanical locks with the individual spaces of the stents to which the stent mounting bodies are mated. When the balloon elements are fully inflated the stent is forced off of the stent mounting bodies as the balloon pushes the stent away from the catheter. The balloon elements will preferably surround and overlap the stent mounting bodies when fully inflated. The fully expanded balloon elements will seat the stent into its final position against the vessel wall.

The balloon elements may be configured to act as individual balloons thereby allowing the operator the ability to expand selected portions of the stent, such as for example, the central portion of the stent first, in order to reduce the potential for flaring along the stent ends. Such selective inflation could also be used to increase pressure on areas of the stent that are interfered with during expansion due to the presence of plaque or other common interferences.

When the balloon elements are deflated the catheter may be withdrawn. The stent mounting bodies may be constructed to be readily flexible or collapsible so as to not interfere with the anatomy of the vessel as the catheter is being wvithdrawn, although this is not necessary.

BRIEF DESCRIPTION OF THE SEVERAL VIEWS OF THE DRAWINGS

A detailed description of the invention is hereafter described with specific reference being made to the drawings in which:

FIG. 1 is a longitudinal view of the distal portion of the present balloon catheter prior to inflation;

FIG. 2 is a longitudinal view of the distal portion of the present balloon catheter after balloon inflation showing the segmented balloons with portions constrained by mounting bodies;

FIG. 3 is a partial side view of a stent receiving portion of a stent mounting body as it would mate with the open structure of a stent;

FIG. 4 is a longitudinal view of an alternative embodiment of the present balloon catheter wherein each balloon element has a separate inflation lumen, and FIG. 5 is a cross sectional view of the central catheter shaft showing the separate inflation lumens for each balloon element, and

DETAILED DESCRIPTION OF THE INVENTION

FIG. 1 shows a longitudinal view of the distal end portion of a first embodiment of the present inventive balloon catheter generally indicated at 10 which includes a stent 20. A central catheter shaft 12 defines an inflation lumen (not shown). Disposed about the central catheter shaft 12 is an uninflated balloon 16 having three balloon elements or segments 16A, 16B, and 16C, each of which are in fluid communication with the inflation lumen. Between each balloon segment is a space within which is a stent mounting body 24, preferably in the form of a disk. The stent mounting bodies extend radially away from the central catheter shaft 12 to a dimension sufficient to receive stent 20 which is disposed thereabout over the balloon segments and crimped thereto as shown at 26. The stent mounting bodies 24 may be configured to mate with the open structures of stent 20. Since the balloon segments are unexpanded, a fold 30 can be seen.

As the balloon elements 16A, 16B, and 16C, are inflated through the inflation lumen, the balloon elements will expand radially and push outwardly against stent 20. As the balloon segments continue to inflate the stent is pushed off of the stent mounting bodies. The pressure exerted by the inflating balloon elements 16A, 16B, and 16C, against stent 20 is sufficient to keep the stent immobilized relative to the length of the catheter and vessel wall.

FIG. 2 shows the balloon elements 16A, 16B, and 16C, being fully inflated with portions constrained under the mounting bodies 24. When inflated the balloon elements may completely surround and overlap the spaces 22 as well as the stent mounting bodies 24. When fully expanded the stent 20 is seated in place i.e. implanted by the force exerted by the balloon elements.

FIG. 3 shows a partial schematic view of stent 20 relative to the stent receiving portion 26 of a disk shaped stent mounting body 24. The stent receiving portion 26 may be configured to mate with the portions of stent 20 as shown. Various embodiments of stent receiving portions on the mounting bodies could include for example, locking ridges, teeth, the use of adhesives to supplement or even replace the stent receiving portion of the stent mounting body, or any other connection and securing means which would be available to one of ordinary skill in the art.

FIG. 4 shows an alternative embodiment of the balloon catheter shown in FIG. 1, wherein each balloon element or segment 16A, 16B, and 16C, is actually a separate balloon with an individually corresponding inflation lumen 14A, 14B, and 14C. Stent 20 is not shown in this figure.

Providing each balloon element with a separate inflation lumen allows the surgeon or operator of the catheter to control the inflation of each balloon element in a unique manner if desired. For example, in order to reduce or prevent stent flaring it may be desirable to inflate balloon elements 16B, prior to 16A and 16C. Such selective inflation would allow the central portion of the stent to expand while leaving the ends of the stent partially unexpanded, thereby preventing the ends from contacting the vessel walls. This function could be enhanced by providing the stent mounting bodies adjacent to the balloon elements 16A and 16C with a greater resistance to release of the stent such as a locking mechanism as has been previously discussed.

FIG. 5 shows the cross sectional view of the balloon catheter as shown in FIG. 4. Each individual inflation lumen 14A, 14B and 14C are contained within the central catheter shaft 12.

As an added safety feature the balloon catheter may be equipped with stent mounting bodies 24 that are collapsible or flexible. Such flexible construction may be employed to ensure that the stent mounting bodies do not interact with other devices that may be present within the vessel or with the vessel itself. Alternatively, a thin retractable sheath or other protective coating may be applied to the balloon catheter.

As the balloon catheter is inserted or withdrawn from a body vessel the radially extended stent mounting bodies 24 may encounter previously implanted medical devices or other interferences within the vessel. As the stent mounting bodies encounter such interference they may be constructed to yieldably bend. In an alternative embodiment the stent mounting bodies may be constructed out of a material of sufficient flexibility to allow the stent mounting bodies to bend as necessary but that will also permit the stent mounting bodies to retain sufficient rigidity to support and guide the stent as described above.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A balloon catheter comprising:
    a plurality of balloon elements carried by the catheter in a stent mounting region, the balloon elements being spaced and arranged longitudinally relative to the catheter in the mounting region, providing at least one space between balloon elements;
    an expandable stent carried over the elements balloon on the catheter, the stent having an unexpanded diameter and an expanded diameter; and
    at least one stent mounting body carried by the catheter and positioned in the at least one space between the balloon elements for securing the stent directly thereto in the unexpanded diameter, the at least one stent mounting body extending radially from the catheter beyond the balloon elements and between the balloon elements and having a predetermined size which is less than the expanded stent diameter.

2. The balloon catheter of claim 1, wherein the balloon elements are segments of a single balloon.

3. The balloon catheter of claim 2, wherein the stent comprises open structures and at least one stent mounting body constructed and arranged to mate with the open structures of the stent.

4. The balloon catheter of claim 2, wherein the balloon segments are constructed and arranged in positions relative to each other so as to close about the stent mounting body upon balloon expansion.

5. The balloon catheter of claim 4, wherein the at least one stent mounting body is further constructed and arranged to form a mechanical lock with the open spaces of a characteristic stent type when the stent is in the unexpanded diameter.

6. A balloon catheter comprising:
a balloon carried by the catheter in a stent mounting region, the balloon being segmented into a plurality of longitudinally spaced segments relative to the catheter in the mounting region, providing a space between each of the individual segments;
an expandable stent carried over the balloon, the stent having an unexpanded diameter and an expanded diameter; and
a plurality of stent mounting bodies each of which is positioned in one of the spaces between segments for securing the stent directly thereto in the unexpanded diameter, the stent mounting bodies extending radially from the catheter beyond the balloon and between the balloon segments and having a predetermined size which is less than the expanded stent diameter.

7. The balloon catheter of claim 6, wherein the stent mounting bodies are of radial form.

8. A balloon catheter comprising:
a balloon carried by the catheter in a stent mounting region, the balloon having a first spaced segment, and a second spaced segment, and a third spaced segment arranged sequentially and longitudinally spaced relative to the catheter in the mounting region, providing a space between each of the individual segments;
an expandable stent carried over the balloon, the stent having open structures, the balloon and stent each having a respective unexpanded diameter and an expanded diameter; and
a first stent mounting body, and a second stent mounting body arranged sequentially, and individually positioned in the spaces between the individual segments for securing the stent in the unexpanded diameter directly thereto, the stent mounting bodies extending radially from the catheter between the balloon segments for a predetermined extent which is less than the expanded stent diameter.

9. The balloon catheter of claim 8, wherein the first spaced balloon segment and the third spaced balloon segments are cone shaped.

10. The balloon catheter of claim 9, wherein the first stent mounting body and the second stent mounting body are constructed and arranged to mate with the open structures of the stent.

11. The balloon catheter of claim 10, wherein the first spaced balloon segment and the third spaced balloon segments are constructed and arranged to expand at a different rate than the second spaced balloon segment.

12. The balloon catheter of claim 10, wherein the second spaced balloon segment has a greater expanded diameter than the first spaced balloon segment and the third spaced balloon segment.

13. The balloon catheter of claim 10, wherein the first stent mounting body and the second stent mounting body are further constructed and arranged to form a mechanical lock with the stent when the stent is in the unexpanded diameter.

14. The balloon catheter of claim 13, wherein the second stent mounting body is constructed and arranged to selectively release the mechanical lock with a portion of the stent prior to the release of the mechanical lock with other portions of the stent by the other mounting bodies.

* * * * *

UNITED STATES PATENT AND TRADEMARK OFFICE
CERTIFICATE OF CORRECTION

PATENT NO. : 6,048,350

DATED : April 11, 2000

INVENTOR(S) : Anthony Vrba

It is certified that error appears in the above-identified patent and that said Letters Patent is hereby corrected as shown below:

Col. 1, line 56, delete "5,647,847" and insert -- 5,647,857 --;

Col. 4, line 55, delete "elements balloon" and insert -- balloon elements --.

Signed and Sealed this

Tenth Day of April, 2001

Attest:

NICHOLAS P. GODICI

Attesting Officer

Acting Director of the United States Patent and Trademark Office